United States Patent [19]

Fujita et al.

[11] Patent Number: 4,495,355

[45] Date of Patent: Jan. 22, 1985

[54] OPTICALLY-ACTIVE DIAMIDE DERIVATIVES

[75] Inventors: Eiichi Fujita, Kyoto; Yoshimitsu Nagao, Uji; Takao Ikeda; Takehisa Inoue, both of Kyoto, all of Japan

[73] Assignee: Yamasa Shoyu Kabushiki Kaisha, Chiba, Japan

[21] Appl. No.: 448,505

[22] Filed: Dec. 9, 1982

[30] Foreign Application Priority Data

Dec. 11, 1981 [JP] Japan ................. 56-200625

[51] Int. Cl.$^3$ ............................................ C07D 41/06
[52] U.S. Cl. ..................................... 546/209; 546/245; 548/188; 548/230; 544/54; 544/55; 544/96; 544/97
[58] Field of Search ..................... 544/54, 55, 96, 97; 546/209, 245; 548/188, 230

[56] References Cited

PUBLICATIONS

Nagao et al. "J. Am. Chem. Soc." (1982) vol. 104, pp. 2079–2081.
Webster's Third New International Dictionary of the English Language Unabridged (Merriam) p. 1130.
Chen et al. "J. Am. Chem. Soc.", vol. 103, pp. 3580–3582 (1981).
Bartlett et al. "J. Am. Chem. Soc.", vol. 102, pp. 337–342 (1980).
Hirama et al. "Tetrahedron Letters", No. 41, pp. 3937–3940 (1979).
Masamune et al. "J. Am. Chem. Soc.", vol. 103, pp. 1568–1571 (1981).
Fukuyama et al. "J. Am. Chem. Soc.", vol. 101, pp. 260–262 (1979).
Collum et al. "J. Am. Chem. Soc.", vol. 102, pp. 2118–2120 (1980).
Kocienski et al. "J. Chem. Soc., Perkin I" (1978) pp. 834–837.
Ohno et al. "J. Am. Chem. Soc.", vol. 103, pp. 2405–2406 (1981).

Primary Examiner—Robert T. Bond
Attorney, Agent, or Firm—Wenderoth, Lind & Ponack

[57] ABSTRACT

A novel optically active diamide derivative represented by the following general formula is provided, which is useful as a starting material for asymmetric synthesis of optically active compounds,

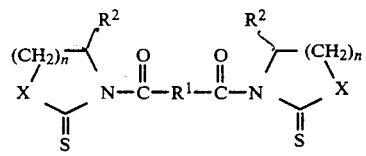

wherein $R^1$ is an acyclic or cyclic, divalent atomic group containing at least one carbon atom which will, upon substitution of one of the heterocyclic groups in the formula with a nucleophilic reagent, stand as an asymmetric center in the substitution product; $R^2$ is a substituent which has such a configuration and a molecular size that the regioselectivity in the substitution reaction of the heterocyclic group with the nucleophilic reagent can be determined by a stereo-chemical interaction thereof with the substituent $R^1$, the steric configuration of the two asymmetric carbon atoms to which the $R^2$ substituents are attached being identical; X is a sulfur atom or an oxygen atom; and n is an integer which is 1 or 2. Such a diamide derivative can be prepared by subjecting the corresponding dicarboxylic acid or an anhydride thereof to a condensation reaction with the corresponding heterocyclic compound in the presence of a condensation agent. The optically-active diamide derivative can be used in the reaction with a nucleophilic reagent to obtain an optically-active compound. The resulting compound can be further modified by subjecting it to reaction with another nucleophilic reagent or to hydrolysis.

6 Claims, 1 Drawing Figure

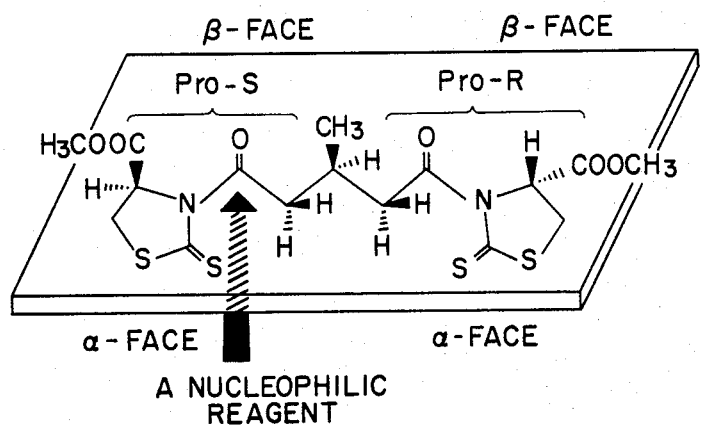

OPTICALLY-ACTIVE DIAMIDE DERIVATIVES

BACKGROUND OF THE INVENTION

This invention relates to novel optically-active diamide derivatives, which are useful as starting materials for asymmetric synthesis of optically active compounds, as well as to production and use thereof.

Acyclic compounds of simple structure having optical activities have recently been recognized to be of ever increasing usefulness because they are very useful as essential starting materials for the preparation of optically active acyclic intermediate compounds to be used in the total synthesis of macrolide antibiotics, macrolactam antibiotics, polyether antibiotics, β-lactam antibiotics, and physiologically active natural substances such as prostaglandin. Some of such optically active acyclic compounds have been produced by either a decomposition of natural substances such as sugars, terpenes, and amino acids or an enzymatic method or chemical asymmetric synthesis.

The highly selective conversion of an enantiotopic group adjacent to the prochiral center in symmetric compounds such as the compounds (1) and (3) below has been attained only by a process utilizing a specified enzyme such as α-chymotrypsin, pig liver esterase, and horse liver alcohol dehydrogenase.

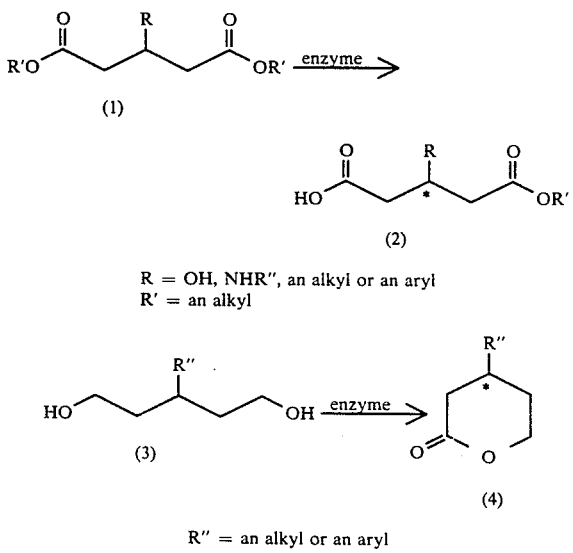

By this enzymatic process, however, only one kind of the enantiomeric isomer can be produced, and moreover, it cannot be predicted which enantiomer can be obtained.

On the other hand, chemical methods can be designed suitably to asymmetrically synthesize only an intended enantiomer. For example, there have been reports of some non-enzymatic processes wherein a nucleophilic reagent is caused to react with an acid anhydride of the above mentioned compound (1) to obtain an optically active compound. These processes, however, are not satisfactory with respect to their optical yields.

SUMMARY OF THE INVENTION

The present invention relates to a method for an asymmetric synthesis which can differentiate with high regioselectivity between two identical functional groups in an acyclic symmetric compound, a meso-cyclic compound and meso-acyclic compound which have prochiral centers. Thus, the present invention seeks to provide novel optically active diamide derivatives useful as starting materials in such an asymmetric synthesis process as well as to provide a process for producing such derivatives and a method for asymmetric synthesis in which such derivatives are utilized. The term "prochiral center" used herein refers to an atom or atomic group which is present in a symmetric compound and acts as an asymmetric center when one of two identical functional groups of the symmetric compound is converted to another functional group.

According to this invention, in one aspect thereof, there is provided an optically active diamide derivative represented by the formula [I],

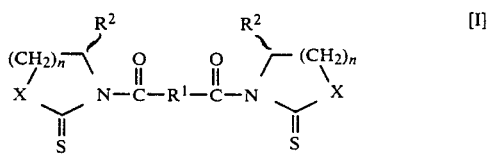

wherein $R^1$ is an acyclic or cyclic, divalent atomic group containing at least one carbon atom which will, upon substitution of one of the heterocyclic groups in formula [I] with a nucleophilic reagent, stand as an asymmetric center in the substitution product; $R^2$ is a substituent which has such a configuration and a molecular size that the regioselectivity in the substitution reaction of the heterocyclic group with the nucleophilic reagent can be determined by a stereo-chemical interaction thereof with the substituent $R^1$, the steric configurations of the two asymmetric carbon atoms to which the $R^2$ substituents are attached being identical; X is a sulfur atom or an oxygen atom; and n is an integer which is 1 or 2.

According to this invention is another aspect thereof, brief summarized, there is provided a process for production of the above described optically active diamide derivative, which process comprises subjecting a specific dicarboxylic acid or the anhydride thereof and a specific heterocyclic compound to condensation reaction in the presence of a condensation agent.

According to this invention is a further aspect thereof, briefly summarized, there are provided methods for reacting the optically active diamide derivative with a nucleophilic reagent to obtain an optically active compound, which can be further subjected to reaction with another nucleophilic reagent, or to hydrolysis.

The nature, utility, and further features of this invention will be more clearly apparent from the following detailed description, commencing with a consideration of general aspects of the invention and concluding with specific examples thereof.

BRIEF DESCRIPTION OF THE DRAWING

In the accompanying drawing, the single FIGURE is a perspective view for schematically illustrating the reactivity of a compound of the present invention with a nucleophilic reagent.

DETAILED DESCRIPTION OF THE INVENTION

Optically Active Diamide Derivatives

The optically active diamide derivative of the present invention is represented by the following formula [I],

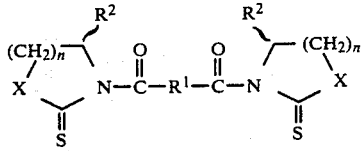

wherein $R^1$ is an acyclic or cyclic, divalent atomic group containing one or more carbon atoms which will, upon substitution of one of the herero-cyclic groups in the formula with a nucleophilic agent, stand as an asymmetric center in the substitution product.

One specific example of such a $R^1$ substituent is represented by the following formula

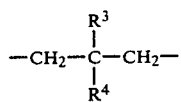

wherein $R^3$ and $R^4$ are atoms or functional groups, respectively, which are different from each other, such as a hydrogen atom, an alkyl group which may have a substituent, an amino group which may have a protecting group, and a hydroxyl group which may have a protecting group.

The alkyl groups include, for example, lower alkyl groups of 1 to 4 carbon atoms such as methyl, ethyl, propyl, isopropyl, n-butyl, isobutyl, and tert-butyl. The substituent to be attached to the alkyl group can be any optional atom or group such as a halogen atom, an alkoxyl group and an aryl group. The protecting group for the amino or hydroxyl group is not especially restricted and can be suitably selected from the groups which are suitable for the synthesis of or reaction of the present compounds. Such protecting groups include, for example, an acyl group such as acetyl, propionyl, butyryl, benzoyl, benzyloxycarbonyl, tert-butyloxycarbonyl and p-methoxybenzyloxycarbonyl, and an ether group such as methoxymethyl, methoxyethoxymethyl, tetrahydrofuryl and tetrahydropyranyl.

Another specific example of such $R^1$ groups is a symmetric substituent represented by the formula,

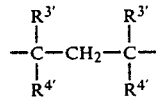

wherein $R^{3'}$ and $R^{4'}$ are functional groups different from each other, respectively, which may be the same as $R^3$ and $R^4$ defined above. Moreover, $R^{3'}$ and $R^{4'}$ may be, for example, single alkylene groups such as ethylene, propylene, and butylene.

Moreover, the $R^1$ can be a mesocyclic substituent represented by the following formulas.

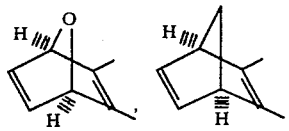

The $R^2$ in the general formula [I] can be a substituent which has such a configuration and a molecular size that the regioselectivity in the substitution reaction of the heterocyclic residue of the present compound with a nucleophilic reagent can be determined by a stereochemical interaction with the substituent $R^1$. Such $R^2$ groups are exemplified by a hydroxyalkyl, alkoxyalkyl, carboxyl, alkoxycarbon, a substitued amidecarbonyl, or alkyl.

The hydroxyalkyl groups include, for example, hydroxymethyl, hydroxyethyl, hydroxypropyl, and hydroxybutyl. The alkoxyalkyl groups include, for example, methoxymethyl, ethoxymethyl, methoxyethyl, and ethoxyethyl. The alkoxycarbonyl carbonyl groups include, for example, methoxycarbonyl, ethoxycarbonyl, propoxycarbonyl, isopropoxycarbonyl, butoxycarbonyl, tert-butoxycarbonyl, benzyloxycarbonyl, and p-methoxybenzyloxycarbonyl. The substituted amidecarbonyl groups include, for example, a mono- or di-alkyl substituted amidecarbonyl group. The alkyl groups include, for example, ethyl, propyl, isopropyl, butyl, isobutyl, and tert-butyl. The absolute configuration of the two asymmetric carbon atoms to which the $R^2$ substituents are attached are identical.

The X in the formula [I] is a sulfur atom or an oxygen atom, and n in the formula [I] is an integer which is 1 or 2.

Production of the Diamide Derivatives

In the preparation of the diamide derivatives of formula [I], a variety of suitable methods can be employed for the formation of the intended bonding and the introduction of atomic groups. More specifically, such a diamide derivative can be prepared by the condensation reaction of a dicarboxylic acid represented by the formula [II] or the anhydride thereof,

with a heterocyclic compound represented by the following formula [III] in the presence of a condensation agent,

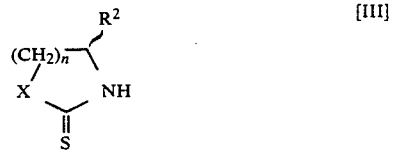

wherein $R^1$, $R^2$, X and n are the same as those of the formula [I].

The moiety $R^1$ in the dicarboxylic acid of the formula [II] is one which provides the moiety $R^1$ in the diamide derivative of the formula [I], but can be defined for the formula [II] independently from the formula [I]. The moiety $R^1$ in the formula [II], which may be alternatively called $R^{1'}$, is an acyclic or cyclic, divalent atomic group containing at least one carbon atom which will, upon substitution of one of the hydroxyl groups in the formula with a nucleophilic reagent, stand as an asymmetric center in the substitution product.

The compounds represented by the formulas [II] and [III] are either known compounds or compounds which can be readily derived from known compounds by conventional chemical processes. For example, of the compounds of the formula [III], a compound wherein $R^2$ is an alkoxycarbonyl group, X is a sulfur atom, n is 1, and the stearic configuration of the carbon atom to which $R^2$ is attached is (R) configuration can be derived by cyclization of an alkyl ester of L-cysteine; and a compound wherein the steric configuration of the carbon atom to which $R_2$ is attached is (S) configuration can be synthesized from an alkyl ester of D-cysteine.

In the case of a compound wherein $R^2$ is an alkoycarbonyl group, n is 1 and X is an oxygen atom, a compound having (R) configuration can be derived from an alkyl ester of L-serine, and a compound having (S) configuration from an alkyl ester of D-serine. In the case of a compound wherein $R^2$ is an alkoxycarbonyl group, X is a sulfur atom and n is 2, a compound having (R) or (S) configuration can be prepared from an alkyl ester of L- or D-homocystein, respectively.

The condensation agent to be used in the condensation reaction is not especially restricted as long as the object of the present process can be attained. More specifically, the condensation agents include, for example, a carboniimide reagent such as dicyclohexylcarbodiimide (DCC), 1-ethyl-3-(3-dimethylaminopropyl)-carbodiimide (EDC), 1-ethyl-3-(3-diethylaminopropyl)-carbodiimide, 1-cyclohexyl-3-(2-morpholinoethyl)-carbodiimide, 1-cyclohexyl-3-(4-diethylaminocyclohexyl)-carbodiimide, and N-methyl-N,N'-ditert-butylcarbodiimidium tetrafluoroborate, as well as N-ethyl-5-phenylisooxazolium-3'-sulfonate (Woodward reagent K).

The reaction is normally carried out in a solvent. As the reaction solvent, conventional solvents that can dissolve the starting compounds and the reaction reagent and do not retard the condensation reaction are used. Examples of such solvents are a solvent of the pyridine series such as pyridine, picoline and lutidine. As the reaction conditions, an anhydrous condition and a temperature in the vicinity of room temperature are used.

The isolation and purification of the present compound of the formula [I] from the reaction mixture thus prepared can be conducted by conventional methods, which can be suitably selected from concentration, dis-solution, precipitation, recrystallization, absorption column chromatography, and the like.

APPLICATION OF THE DIAMIDE DERIVATIVES

The optically active diamide derivatives of the present invention are very useful as starting materials for the asymmetric synthesis of optically active acyclic intermediates in the synthesis of various physiologically active natural substances.

The diamide derivative represented by the formula [I] will be further described with respect to a typical diamide compound having the following structural formula (A), wherein $R^1$ is a

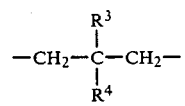

group, $R^3$ is methyl $R^4$ is hydrogen $R^2$ is methoxycarbonyl of (R) configuration, X is sulfur and n is 1.

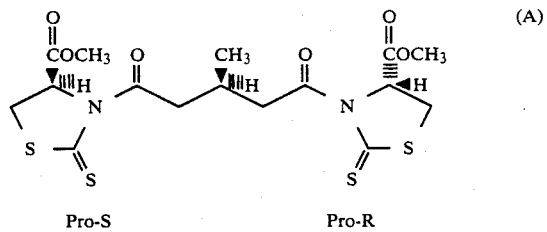

In a low temperature condition, the compound (A) is controlled stereochemically by the action of the considerably strong dipole-dipole repulsion between the thiocarbonyl group and the amidecarbonyl group and the repulsion between the Pro-S group and the Pro-R group, and thus is stabilized as a W-shape conformation (cf. FIG. 1). In such an assumed W-shape conformation, the α-face of the Pro-S ligand has the least steric hindrance in comparison with the other three faces (i.e., β-face of the Pro-S, and α- and β- faces of the Pro-R). Thus, a suitable nucleophilic reagent can preferentially attack, in its transition state, the amidecarbonyl carbon of the Pro-S side from the α- face having the least steric hindrance.

On the basis of this principle, the substitution reaction of one of the heterocyclic residue groups of the present compound of the formula [I] with a nucleophilic regent can be conducted with high regioselectivity by the reaction of the present compound with the nucleophilic reagent ($Nu^1$). Moreover, the substitution of the remaining heterocyclic residue group with the second nucleophilic reagent ($Nu^2$) can be further conducted by treating the product of the first nucleophilic substitution reaction with the second nucleophilic reagent. In accordance with the present invention, it is thus possible to readily introduce a desired atomic group into either of the amidocarbonyl groups of the present compound of the formula [I]. In this connection, the by-product in the first reaction stage is a diastereomer of the main product and thus is readily separated from the main product.

Especially in the compounds of the present invention, a compound wherein $R^1$ is a

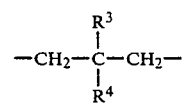

group and $R^3$ or $R^4$ is an amino group which may be substituted can be used as the starting material for the synthesis of a β-lactam.

In the method for asymmetric synthesis utilizing the compounds of the present invention, a variety of nucleophilic reagents can be used. The nucleophilic reagent should be suitably selected according to the aim of the synthesis. The nucleophilic reagents to be used include, for example, alkylamines, cycloalkylamines, aralkylamines, arylamines, aryl thiols, alkyl thiols, alkyl cyanides, as well as active methylene compounds such as an acetoacetate ester and a malonate ester, and the like. It is preferable that these nucleophilic reagents be more nucleophilic than the heterocyclic groups in the formula [I] compounds.

The reaction is normally carried out in a solvent. As the reaction solvent, conventional solvents which can dissolve the starting compounds and the reaction reagent and do not retard the reaction are used. The solvents to be used can be suitably selected from halohydrocarbons (e.g., dichloromethane, chloroform), aromatic hydrocarbons (e.g., benzene, toluene), alcohols, ethers (e.g., ethyl ether, dioxane, tetrahydrofuran, diglyme), organic esters, amide solvents, dimethylsulfoxide, sulfolane, and the like. The reaction is preferably conducted under a mild reaction condition at a low temperature, for example, at a temperature of $-50°$ C. to room temperature.

By the reaction with the first nucleophilic reagent ($Nu^1$), an optically active compound represented by the formula [IV] can be obtained,

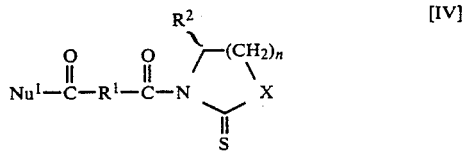

wherein $Nu^1$ stands for the residue from the nucleophilic reagent used, and $R^1$, $R^2$, X and n are as defined hereinbefore. The regioselectivity of the $Nu^1$ is determined by the stereochemical interaction between the substituents $R^1$ and $R^2$ and the formula [I] compound.

By subjecting the compound of the formula [IV] thus obtained to reaction with the second nucleophilic reagent ($Nu^2$), an optically active compound represented by the following formula [V] can be synethesized,

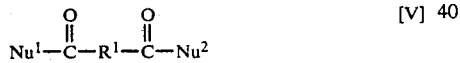

wherein $Nu^1$ and $Nu^2$ stand for the residues from the first and second nucleophilic reagents used, respectively, and $R^1$ is as defined hereinbefore.

Moreover, an optically active compound represented by the formula [VI] can be obtained by subjecting the compound of the formula [IV] described above to hydrolysis,

wherein $Nu^1$ and $R^1$ are as defined hereinbefore. The hydrolysis reaction is carried out under such a weak base condition that the $Nu^1$ residue group is not released, for example, in a pyridine-water medium.

The isolation and purification of the optically active compounds prepared by the asymmetric synthesis processes of the present invention can be conducted according to conventional methods.

In order to indicate more fully in concrete terms the nature and utility of this invention, the following specific examples of practice relating to the compounds of this invention, the production thereof, and practical application of asymmetric synthesis with the use thereof are set forth, it being understood that these examples are presented as illustrative only and are not intended to limit the scope of the invention.

EXAMPLE 1

In 110 ml of pyridine were dissolved 5.54 g of 3-methylglutaric acid and 14.18 g of 4(R)-methoxycarbonyl-1,3-thiazolidine-2-thione (hereinafter referred to as 4(R)-MCTT), to which 18.16 g of dicyclohexylcarbodiimide (hereinafter referred to as DCC) was added. The mixture was dissolved with stirring and subjected to reaction at room temperature for 6 days.

After termination of the reaction, pyridine was removed under reduced pressure, the resulting residue was dissolved in ethyl acetate, insoluble material being filtered off. Ethyl acetate was distilled off under reduced pressure; the resulting residue was dissolved in ethyl ether; and yellow crystals thus separated were collected. The yellow crystals were recrystallized from ethyl acetate to obtain 13.0 g of 4(R)-MCTT diamide of 3-methylglutaric acid as yellow needle-like crystals in a yield of 69.9%.

Structural formula:

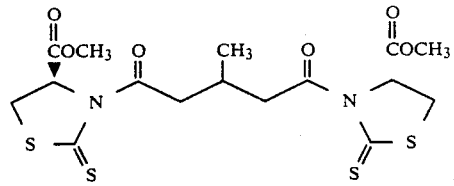

Melting point: 113° to 114° C.

Specific rotation: $[\alpha]_D^{25} -163.90°(c=1.00,$ ethyl acetate).

Elemental analysis: as $C_{16}H_{20}N_2O_6S_4$.

|  | C | H | N | S |
|---|---|---|---|---|
| Calculated: | 41.38 | 4.35 | 6.03 | 27.61 |
| Found: | 41.36 | 4.32 | 5.83 | 27.48 |

Nuclear magnetic resonance spectrum: $(CDCl_3)\delta(ppm)$ (hereinafter referred to as NMR spectrum): 5.48–5.65, m, 2H, 3.82, s, 6H, 3.1–3.82, m, 8H, 2.64–2.84, m, 1H, 1.08, d 3H.

EXAMPLE 2

In 30 ml of pyridine were dissolved 3.15 g of 3-acetylaminoglutaric acid and 3.15 g of 4(R)-MCTT, to which 4.4 g of DCC was added. The mixture was subjected to reaction at room temperature for 5 days.

After terminationof the reaction, pyridine was distilled off under reduced pressure; the resulting residue was dissolved in chloroform; and insoluble material was filtered off. The resulting chloroform solution was then separated and purified by means of silica gel column chromatography (eluting agent, ethyl acetate). The product was recrystallized from ethyl acetate to obtain 3.1 g of 4 (R)-MCTT diamide of 3-acetylaminoglutaric acid in a yield of 71%.

Structural formula:

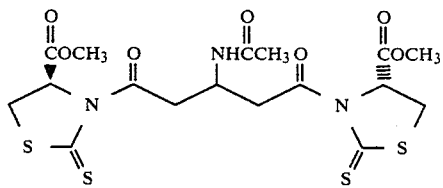

Melting point: 163° to 164° C.
Specific rotation: $[\alpha]_D^{18}$ −0.3°(c=1.02, chloroform).
NMR spectrum: (CDCl$_3$)δ(ppm). 6.24, br.d, 1H, 5.7–5.5, m, 2H, 4.64–5.0, m, 1H, 3.26–3.98, m, 1.94, s, 3H.

EXAMPLE 3

In 100 ml of pyridine were dissolved 10.2 g of 3-[1-(2′-methoxy-ethoxy)-methoxyl]-glutaric acid (hereinafter referred to as 3-MEMG) and 9.2 g of 4(R)-MCTT, after which 11.8 g of DCC was added. The mixture was subjected to reaction with stirring at room temperature of 6 days. Then, pyridine was distilled off under reduced pressure, and 100 ml of chloroform was added to the residue. The mixture was further subjected to reaction with stirring at room temperature for 1 day.

After termination of the reaction, insoluble material was filtered off, and then chloroform was distilled off. The resulting residue was separated and purified by silica gel column chromatography (eluting agent, a 5:1 mixture of benzene and ethyl acetate) to obtain 9.31 g of 4(R)-MCTT diamide of 3-MEMG as yellow syrup in a yield of 64%.

Structural formula:

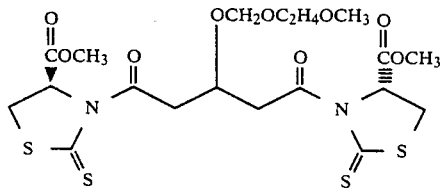

Specific rotation: $[\alpha]_D^{25}$ −129.9° (c=1.01, chloroform).
Mass analysis spectrum: m/e 465 (M+).
NMR spectrum: (CDCl$_3$)δ(ppm). 5.09–5.50, m, 2H, 4.77, s, 2H, 3.80, s, 6H, 3.36, s, 3H, 3.28–3.96, m, 9H.

EXAMPLE 4

In 50 ml of pyridine were dissolved 0.98 g of meso-2,4-dimethylglutaric anhydride and 2.4 g of 4(R)-MCTT, and then 2.8 g of DCC was added thereto. The mixture was subjected to reaction with stirring at room temperature for 4 days.

After termination of the reaction, pyridine was distilled off under reduced pressure. The resulting yellow syrup was dissolved in chloroform, and insoluble material was filtered off. Then chloroform was distilled off under reduced pressure. The residual yellow syrup was separated and purified by silica gel column chromatography (eluting agent, a 10:1 mixture of benzene and ethyl acetate) to obtain 2.8 g of 4(R)-MCTT diamide of 2,4-dimethylglutaric acid as a yellow oily substance in a yield of 85%.

Structural formula:

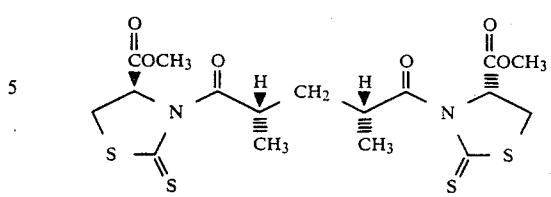

Specific rotation: $[\alpha]_D^{25}$ −169.2° (c=1.05, chloroform).
Mass analysis spectrum: m/e 478 (M+).
NMR spectrum: (CDCl$_3$) δ(ppm) 5.45–5.68, m, 2H, 4.73–4.80, m, 2H, 3.80, s, 3H, 3.76, s, 3H, 3.23–3.86, m, 4H, 1.62, q, 2H, 1.29, d, 3H, 1.17, d, 3H.

EXAMPLE OF APPLICATION 1

In 300 ml of dichloromethane was dissolved 10 g of 4(R)-MCTT diamide of 3-methylglutaric acid. The resulting solution was cooled with dry ice-acetone in a nitrogen stream. Into the mixture under stirring, a solution of 1.83 g piperidine in 30 ml dichloromethane was poured. The resulting mixture was allowed to react at −30° C. for 4 hours.

The reaction mixture was allowed to assume room temperature, and the dichloromethane solvent was distilled off. The resulting residue was separated and purified by silica gel column chromatography (eluting agent, a 2:2:1 mixture of n-hexane, ethyl acetate and ethyl ether). The product was recrystallized from ethyl acetate to obtain 4.3 g of 1-[4(R)-MCTT]-3(R)-methyl-5-piperidylpentane-1,5-dione (hereinafter referred to as compound (R) ] in a yield of 61.6%.

Structural formula

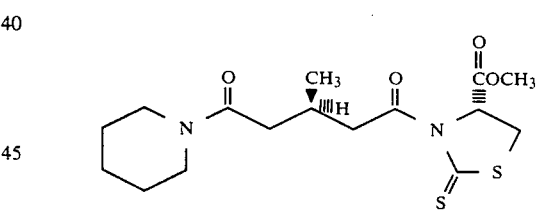

Melting point: 95.5° to 96.0° C.
Mass analysis spectrum: m/e 372 (M+).
Elemental analysis: $C_{16}H_{24}N_2O_4S_2$.

|  | C | H | N | S |
| --- | --- | --- | --- | --- |
| Calculated: | 51.60 | 6.50 | 7.52 | 17.22 |
| Found: | 51.41 | 6.62 | 7.47 | 17.37 |

NMR spectrum: (CDCl$_3$)δ(ppm). 5.62, q, 1H, 3.85, s, 3H, 3.06–3.85, m, 8H, 2.06–2.8, m, 3H, 1.3–1.7, m, 6H, 1.04, d, 3H.

From another eluted fraction of the silica gel column chromatography, 0.58 g of 1-[4(R)-MCTT]-3(S)-methyl-5-piperidylpentane-1,5-dione [hereinafter referred to as compound (S)] was obtained as a yellow oily substance in a yield of 8.3%.

Structural formula:

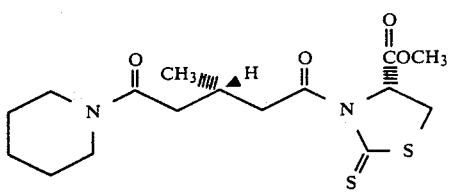

Specific rotation: $[\alpha]_D^{18}-84.67°$ (c=1.54, chloroform).

Mass analysis spectrum: m/e 372 ($M^{30}$).

NMR spectrum: $(CDCl_3)\delta$(ppm). 5.62, q, 1H, 3.82, s, 3H, 3.2-3.9, m, 8H, 2.0-2.68, m, 3H, 1.3-1.7, m, 6H, 1.07, d, 3H.

EXAMPLE OF APPLICATION 2

In 10 ml of dichloromethane was dissolved 200 mg of the compound (R), to which 63 mg of benzyl amine was added at room temperature under stirring. The mixture was allowed to react for 10 minutes.

Dichloromethane was distilled off under reduced pressure from the reaction mixture. The resulting residue was separated and purified by silica gel column chromatography (eluting agent, a 5:1 mixture of chloroform and methanol). The product was recrystallized from ethyl ether to obtain 159 mg of 1-benzylamino-3(S)-methyl-5-piperidylpentane-1, 5-dione as white needle-like crystals in a yield of 98%.

Structural formula:

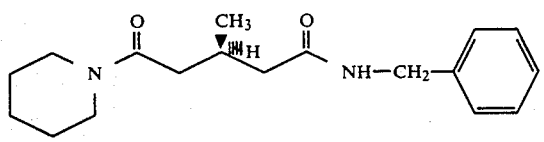

Melting point: 77°-78.5° C.
Specific rotation: $[\alpha]_D^{25}-2.9°$ (c=1.00, chloroform).
Elemental analysis: as $C_{18}H_{26}O_2N_2$.

|  | C | H | N |
|---|---|---|---|
| Calculated: | 71.49 | 8.67 | 9.26 |
| Found: | 71.20 | 8.80 | 9.24 |

EXAMPLE OF APPLICATION 3

The compounds represented by the following structural formula were obtained from the compound (R) and an amine by carrying out a reaction as in Example of Application 2. The $Nu^2$ substituents and properties of the compounds are shown in Table 1.

TABLE 1

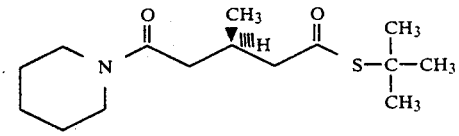

| Compound | $Nu^2$ substituent | Specific rotation (25° C., chloroform) | Melting point (°C.) |
|---|---|---|---|
| a | —NH—CH(CH₃)(H)(Ph) | −63.48° (C = 0.66) | 155-155.5 |
| b | —NH—CH(CH₃)(H)(Ph) | +51.67° (C = 0.66) | 92-92.5 |
| c | —NH—C₆H₄—Br | +0.98° (C = 1.02) | 124-125 |

EXAMPLE OF APPLICATION 4

In a nitrogen stream, 129 mg of 50% sodium hydride-oil suspension was suspended in 5 ml of tetrahydrofuran. Into this suspension, a solution of 0.3 g of tert-butyl thiol in 2 ml of tetrahydrofuran was poured in a nitrogen stream, and the resulting mixture was stirred for 1 hour.

A solution of 0.5 g of the compound (R) in 3 ml of tetrahydrofuran was poured into the solution prepared as described above. The mixture was subjected to reaction for 2 hours under stirring.

Then, 0.3 ml of glacial acetic acid was added to the resulting reaction mixture, and the solvent was distilled off under reduced pressure. The residue was separated and purified by silica gel column chromatography (eluting agent, a 5:1 mixture of n-hexane and ethyl acetate). An oily compound thus obtained was further purified by distillation to produce 0.327 g of 1-piperidyl-3(R)-methyl-5-tert-butylthiopentane-1,5-dione in a yield of 85.4%.

Structural formula:

Specific rotation: $[\alpha]_D^{23}-4.02°$ (c=1.32, chloroform).
Mass analysis spectrum: m/e 285 ($M^+$).
Elemental analysis: as $C_{15}H_{27}NO_2S$

|  | C | H | N | S |
|---|---|---|---|---|
| Calculated: | 63.13 | 9.54 | 4.91 | 11.22 |
| Measured: | 62.75 | 9.80 | 4.73 | 11.24 |

NMR spectrum: $(CDCl_3)\delta$(ppm). 3.3-3.62, m, 4H, 2.04-2.62, m, 5H, 1.25-1.75, m, 6H, 1.26, s, 9H, 1.02, d, 3H.

EXAMPLE OF APPLICATION 5

The compounds represented by the following structural formula were obtained from the compound (R) and a nucleophilic reagent by carrying out a reaction as in Example of Application 4. The Nu² substituents and properties of the compounds are shown in Table 2.

TABLE 2

| Compound | Nu² substituent | Specific rotation (25° C. chloroform) | Melting point (°C.) |
|---|---|---|---|
| d | —S—⟨⟩—Br | −1.39° | Oily |
| e | —CH=S(CH₃)₂ (with O above S) | +2.30° | 130–131.5 |
| f | —CH(COOC₂H₅)₂ | −3.63° | Oily |

EXAMPLE OF APPLICATION 6

In 3 ml of dichloromethane was dissolved 107 mg of the compound (S), to which 37 mg of D-phenylethylamine was added. The mixture was subjected to reaction at room temperature for 30 minutes.

After termination of the reaction, dichloromethane was distilled off under reduced pressure. The resulting residue was separated and purified by silica gel column chromatography (eluting agent, a 20:1 mixture of chloroform and methanol). The product was recrystallized from ethyl acetate to obtain 78 mg of 3(R)-methyl-1-[1(R)-methylbenzylamino]-5-piperidylpentane-1,5-dione as white prism crystals in a yield of 85.8%.

Structural formula:

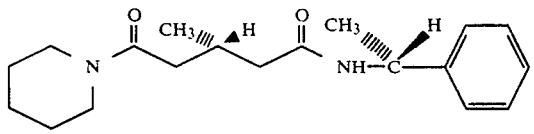

Melting point: 155°–155.5° C.

Specific rotation: $[\alpha]_D^{23}$ +63.19 (c=0.69, chloroform).

Mass analysis spectrum: m/e 316 (M⁺).

NMR spectrum: (CDCl₃)δ(ppm). 7.1–7.36, m, 5H, 6.68, br.d, 1H, 5.1, m, 1H, 3.2–3.6, m, 4H, 2.10–2.48, m, 5H, 1.4–1.7, m, 6H, 1.28, d, 3H, 1.04, d, 3H.

EXAMPLE OF APPLICATION 7

5 ml of water was added to a solution of 0.5 g of piperidine.4(R)-MCTT diamide in 5 ml of pyridine. The mixture was subjected to reaction at room temperature for 15 hours.

After termination of the reaction, pyridine and water were removed under reduced pressure. The resulting oily residue was separated and purified by silica gel column chromatography (eluting agent: a 3:1 mixture of chloroform and methanol) to obtain 0.264 g of oily 3(R)-methyl-5-oxo-5-piperidylpentanoic acid in a yield of 92.3%.

Structural formula:

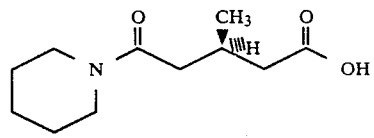

Specific rotation: $[\alpha]_D^{25}$ −6.19 (c=4.54, chloroform).

Mass analysis spectrum: m/e 213 (M⁺).

NMR spectrum: (CDCl₃)δ(ppm). 10.66, s, 1H, 3.3–3.7, m, 4H, 2.2–2.7, m, 5H, 1.4–1.8, m, 6H, 1.06, d, 3H.

EXAMPLE OF APPLICATION 8

12 g of 4(R)-MCTT diamide of meso-2,4-dimethylglutaric acid was dissolved in 150 ml of dichloromethane. Into this solution, 31 ml of a solution of 3 g of piperidine in 40 ml of dichloromethane was added dropwise at −30° C., and, one hour thereafter, the temperature of the solution was gradually raised to 0° C., at which the solution was agitated for 2 hours.

From the reaction mixture, the solvent was distilled off, and the residue was separated and purified by silica gel column chromatography (eluting agent: benzene→benzene: ethyl acetate=9:1). By recrystallization from dichloromethane-ethylether and dichloromethane-petroleum ether, 4.9 g of piperidine.4(R)-MCTT diamide of meso-2,4-dimethylglutaric acid (hereinafter referred to by the abbreviated designation compound (T)) was obtained in a yield of 47.6%.

Structural formula:

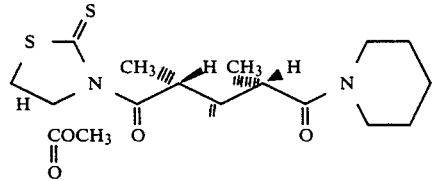

Melting point: 111°–112° C.

Mass analysis spectrum: m/e 386 (M⁺).

Specific rotation: $[\alpha]_D^{20}$ −113.79 (c=1.095, chloroform).

NMR spectrum: (CDCl₃, 100 MHz)δ(ppm). 5.69, q, 1H (J=2.20, 8.40 Hz), 4.35–4.55, m, 1H, 3.81, s, 3H, 3.29–3.77, m, 6H, 2.65–2.86, m, 1H, 2.04–2.33, m, 1H, 1.36–1.62, m, 7H, 1.27, d, 3H (J=6.84 Hz), 1.07, d, 3H (J=6.60 Hz).

It was confirmed by HPLC analysis that the formation ratio of the compound (T) and a compound of the structural formula

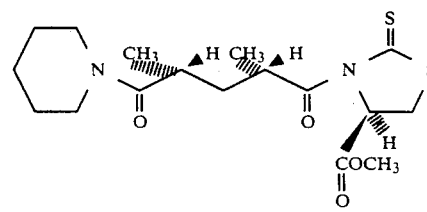

in the instant reaction was 97.5:2.5.

Melting point: 135° to 135.5° C.

Mass analysis spectrum: m/e 386 (M+).
Specific rotation: $[\alpha]_D^{25} -46.35$ (c=1.620, chloroform).

lowing structural formula with the $Nu^2$ substituents indicated in Table 3 were obtained.

TABLE 3

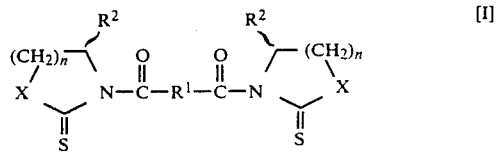

| Compound | Nucleophile | $Nu^2$ substituent | Specific rotation (25° C. chloroform) | Melting point (°C.) | Yield (%) |
|---|---|---|---|---|---|
| g | CH₃—S—CH₂ with CH₃⊕ (NaH) | CH₃—S—CH— with CH₃⊕ | −19.08 (c = 1.09) | 110–111 | 94.0 |
| h | (enolate Mg—Br complex with C₂H₅O groups) | C₂H₅O—C(O)—CH₂— | +5.90 (c = 2.03) | Oily | 79.1 |
| i | Br—C₆H₄—SH | Br—C₆H₄—S— | −9.95 (c = 1.19) | Oily | 98.7 | form).

EXAMPLE OF APPLICATION 9

386 mg of the compound (T) was dissolved in 5 ml of dichloromethane. Into the resulting solution, 5 mll of a solution of 145 mg of R(+)-α-methylbenzylamine in 5 ml of dichloromethane was added dropwise, and the resulting mixture was agitated at room temperature for 30 minutes.

The solvent was distilled off from the reaction mixture to leave a residue, and then the residue was separated and purified twice by silica gel column chromatography (eluting agent: (first cycle) benzene: ethyl acetate = 10:1→benzene: ethyl acetate = 1:1, (second cycle) benzene: ethyl acetate = 7:3). As a result, 308 mg of piperidine.R(+)-α-methylbenzylamine diamide of meso-2,4-dimethylglutaric acid was obtained in a yield of 93.3% as a colorless oily substance.

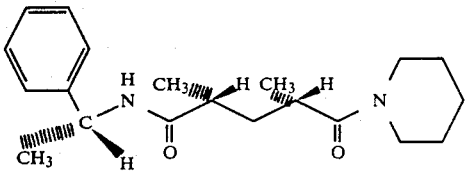

Mass analysis spectrum: m/e 330 (M+).
Specific rotation: $[\alpha]_D^{25} +57.66$ (c=1.07, chloroform).

EXAMPLE OF APPLICATION 10

In accordance with the foregoing Examples of Application, various nucleophiles were allowed to react with the compound (T), whereupon compounds of the fol-

What is claimed is:
1. An optically active diamide of the formula

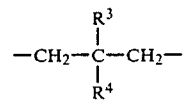

wherein $R^1$ is a divalent group which will, upon substitution of one of the heterocyclic groups in formula I with a nucleophilic reagent, stand as an asymmetric center in the substitution product, said $R^1$ being selected from the group consisting of (1) a group of the formula $$-CH_2-\underset{\underset{R^4}{|}}{\overset{\overset{R^3}{|}}{C}}-CH_2-$$

wherein $R^3$ and $R^4$ are different from each other and are selected from the group consisting of hydrogen; alkyl of 1–4 carbon atoms which may be substitued by halogen, alkoxyl or aryl; amino which may be protected by acetyl, propionyl, butyryl, benzoyl, benzyloxycarbonyl, tert-butyloxycarbonyl, p-methoxybenzyloxycarbonyl, methoxymethyl, methoxyethoxymethyl, tetrahydrofuryl or tetrahydropyranyl; and hydroxyl which may be protected by one of said amino-protecting groups, (2) a group of the formula

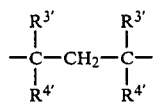

wherein R$^{3'}$ and R$^{4'}$ are different from each other and have the same meanings as R$^3$ and R$^4$ defined above, or R$^{3'}$ and R$^{4'}$ may together form an ethylene, propylene or butylene group, (3) a group of the formula

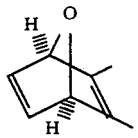

and (4) a group of the formula

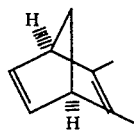

R$^2$ is a substituent which has such a configuration and a molecular size that the regioselectivity in the substitution reaction of the heterocyclic residue in the formula I with a nucleophilic reagent can be determined by a stereochemical interaction with the substituent R$^1$, said R$^2$ being selected from the group consisting of hydroxyalkyl of 1–4 carbom atoms, alkoxyalkyl of 2–4 carbon atoms, carboxyl, alkoxycarbonyl of 2–9 carbon atoms, a mono- or di-alkyl substituted amidecarbonyl group, and alkyl of up to 4 carbon atoms the steric configuration of the two asymmetric carbon atoms to which the R$^2$ substituents are attached being identical, X is sulfur or oxygen, and n is an integer which is 1 or 2.

2. A process for producing an optically active diamide of the formula

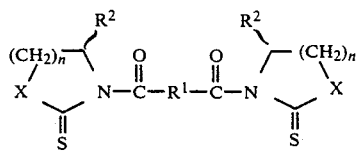 [I]

wherein R$^1$ is a divalent group which will, upon substitution of one of the heterocyclic groups in formula I with a nucleophilic reagent, stand as an asymmetric center in the substitution product, said R$^1$ being selected from the group consisting of (1) a group of the formula

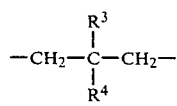

wherein R$^3$ and R$^4$ are different from each other and are selected from the group consisting of hydrogen; alkyl of 1–4 carbon atoms which may be substituted by halogen, alkoxyl or aryl; amino which may be protected by acetyl, propionyl, butyryl, benzoyl, benzyloxycarbonyl, tert-butyloxycarbonyl, p-methoxybenzyloxycarbonyl, methoxymethyl, methoxyethoxymethyl, tetrahydrofuryl or tetrahydropyranyl; and hydroxyl which may be protected by one of said amino-protecting groups, (2) a group of the formula

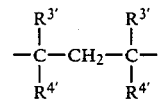

wherein R$^{3'}$ and R$^{4'}$ are different from each other and have the same meanings as R$^3$ and R$^4$ defined above, or R$^{4'}$ and R$^{4'}$ may together form an ethylene, propylene or butylene group, (3) a group of the formula

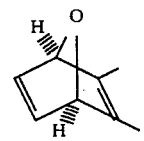

and (4) a group of the formula

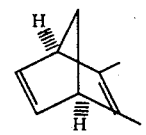

R$^2$ is a substituent which has such a configuration and a molecular size that the regioselectivity in the substitution reaction of the heterocyclic residue in formula I with a nucleophilic reagent can be determined by a stereochemical interaction with the substituent R$^1$, said R$^2$ being selected from the group consisting of hydroxyalkyl of 1–4 carbon atoms, alkoxyalkyl of 2–4 carbon atoms, carboxyl, alkoxycarbonyl of 2–9 carbon atoms, a mono- or di-alkyl substituted amidecarbonyl group, and alkyl of up to 4 carbon atoms, the steric configuration of the two asymmetric carbon atoms to which the R$^2$ substituents are attached being identical, X is sulfur or oxygen, and n is an integer which is 1 or 2, which process comprises subjecting a dicarboxylic acid of the formula

 [II]

wherein R$^1$ is as defined above, or an anhydride thereof, and a heterocyclic compound of the formula

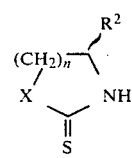 [III]

wherein $R^2$, X and n are as defined above, to a condensation reaction in the presence of a condensation agent.

3. A process for producing an optically active compound which comprises reacting an optically active diamide of the formula

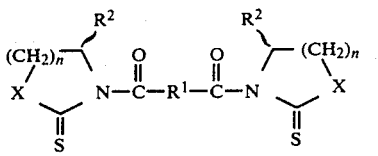

wherein $R^1$ is a divalent group which will, upon substitution of one of the heterocyclic groups in formula I with a nucleophilic reagent, stand as an asymmetric center in the substitution product, said $R^1$ being selected from the group consisting of (1) a group of the formula

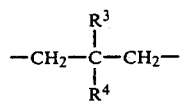

wherein $R^3$ and $R^4$ are different from each other and are selected from the group consisting of hydrogen; alkyl of 1-4 carbon atoms which may be substituted by halogen, alkoxyl or aryl; amino which may be protected by acetyl, propionyl, butyryl, benzoyl, benzyloxycarbonyl, tert-butyloxycarbonyl, p-methoxybenzyloxycarbonyl, methoxymethyl, methoxyethoxymethyl, tetrahydrofuryl or tetrahydropyranyl; and hydroxyl which may be protected by one of said amino-protecting groups, (2) a group of the formula

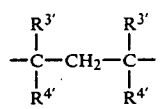

wherein $R^{3'}$ and $R^{4'}$ are different from each other and have the same meanings as $R^3$ and $R^4$ defined above, or $R^{3'}$ and $R^{4'}$ may together form an ethylene, propylene or butylene group, (3) a group of the formula

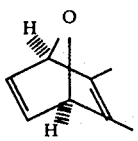

and (4) a group of the formula

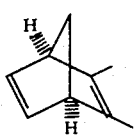

$R^2$ is a substituent which has such a configuration and a molecular size that the regioselectivity in the substitution reaction of the heterocyclic residue in formula I with a nucleophilic reagent can be determined by a stereochemical interaction with the substituent $R^1$, and $R^2$ being selected from the group consisting of hydroxyalkyl of 1-4 carbon atoms, alkoxyalkyl of 2-4 carbon atoms, carboxyl, alkoxycarbonyl of 2-9 carbon atoms, a mono- or di-alkyl substituted amidecarbonyl group, and alkyl of up to 4 carbon atoms, the steric configuration of the two asymmetric carbon atoms to which the $R^2$ substituents are attached being identical, X is sulfur or oxygen, and n is an integer which is 1 or 2, with a nucleophilic reagent to produce an optically active compound of the formula

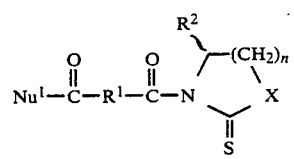

wherein $Nu^1$ is a residue from the nucleophilic reagent, and $R^1$, $R^2$, X and n are as defined above.

4. A process for producing an optically active compound which comprises reacting an optically active diamide of the formula

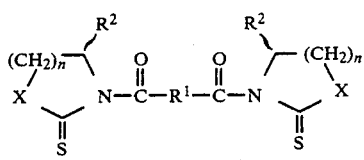

wherein $R^1$ is a divalent group which will, upon substitution of one of the heterocyclic groups in formula I with a nucleophilic reagent, stand as an asymmetric center in the substitution product, said $R^1$ being selected from the group consisting of (1) a group of the formula

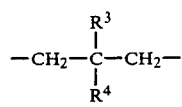

wherein $R^3$ and $R^4$ are different from each other and are selected from the group consisting of hydrogen; alkyl of 1-4 carbon atoms which may be substituted by halogen, alkoxyl or aryl; amino which may be protected by acetyl, propionyl, butyryl, benzoyl, benzyloxycarbonyl, tert-butyloxycarbonyl, p-methoxybenzyloxycarbonyl, methoxymethyl, methoxyethoxymethyl, tetrahydrofuryl or tetrahydropyranyl; and hydroxyl which may be protected by one of said amino-protecting groups, (2) a group of the formula

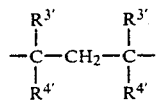

wherein $R^{3'}$ and $R^{4'}$ are different from each other and have the same meanings as $R^3$ and $R^4$ defined above, or $R^{3'}$ and $R^{4'}$ may together form an ethylene, porpylene or butylene group, (3) a group of the formula

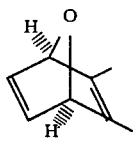

and (4) a group of the formula

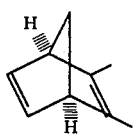

R² is a substituent which has such a configuration and a molecular size that the regioselectivity in the substitution reaction of the heterocyclic residue in formula I with a nucleophilic reagent can be determined by a sterochemical interaction with the substutuent R¹, said R² being selected from the group consisting of hydroxyalkyl of 1-4 carbon atoms, alkoxyalkyl of 2-4 carbon atoms, carboxyl, alkoxycarbonyl of 2-9 carbon atoms, a mono- or di-alkyl substituted amidecarbonyl group, and alkyl of up to 4 carbon atoms, the steric configuration of the two asymmetric carbon atoms to which the R² substituents are attached being identical, X is sulfur or oxygen, and n is an integer which is 1 to 2, with a first nucleophilic reagent to produce an optically active compound of the formula

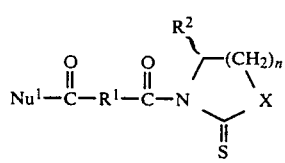

wherein Nu¹ is a residue from the first nucleophilic reagent, and R¹, R², X and n are as defined above, and reacting the compound of the formul with a second nucleophilic reagent to produce an optically active compound of the formula

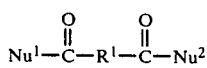

wherein each of Nu¹ and Nu² is a residue from the first and the second nucleophilic reagents, respectively, and R¹ is as defined above.

5. A process for producing an optically active compound which comprises reacting an optically active diamide of the formula

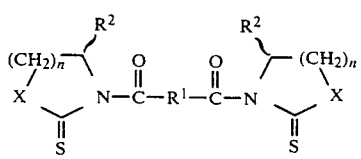

wherein R¹ is a divalent group which will, upon substitution of one of the heterocyclic groups in formula I with a nucleophilic reagent, stand as an asymmetric center in the substitution product, said R¹ being selected from the group consisting of (1) a group of the formula

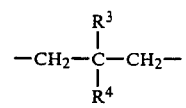

wherein R³ and R⁴ are different from each other and are selected from the group consisting of hydrogen; alkyl of 1-4 carbon atoms which may be substituted by halogen, alkoxyl or aryl; amino which may be protected by acetyl, propionyl, butyryl, benzoyl, benzyloxycarbonyl, tert-butyloxycarbonyl, p-methoxybenzyloxycarbonyl, methoxymethyl, methoxyethoxymethyl, tetrahydrofuryl or tetrahydropyranyl; and hydroxyl which may be protected by one of said amino-protecting groups, (2) a group of the formula

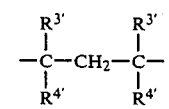

wherein R³' and R⁴' are different from each other and have the same meanings as R³ and R⁴ defined above, or R³' and R⁴' may together form an ethylene, propylene or butylene group, (3) a group of the formula

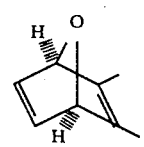

and (4) a group of the formula

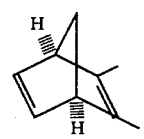

R² is a substituent which has such a configuration and a molecular size that the regioselectivity in the substitution reaction of the heterocyclic residue in formula I with a nucleophilic reagent can be determined by a stereochemical interaction with the substituent R¹, said R² being selected fromm the group consisting of hydroxyalkyl of 1-4 carbon atoms, alkoxyalkyl of 2-4 carbon atoms, carboxyl, alkoxycarbonyl of 2-9 carbon atoms, a mono- or di-alkyl substituted amidecarbonyl group, and alkyl of up to 4 carbon atoms, the steric configuration of the two asymmetric carbon atoms to which the R² substituents are attached being identical, X is sulfur or oxygen, and n is an integer which is 1 or 2, with a nucleophilic reagent to produce an optically active compound of the formula

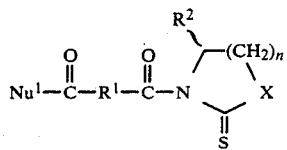
wherein $Nu^1$ is a residue from the nucleophilic reagent, and $R^1$, $R^2$, X and n are as defined above, and subjecting the compound of the formula to hydrolysis to produce an optically active compound of the formula
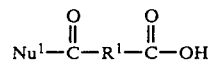
wherein $Nu^1$ and $R^1$ are as defined above.
6. A process as claimed in claim 5 wherein the hydrolysis is conducted in a pyridine-water medium.
* * * * *